(12) United States Patent
Tian et al.

(10) Patent No.: US 12,370,130 B1
(45) Date of Patent: Jul. 29, 2025

(54) PREPARATION METHOD FOR POWDER PRODUCT, POWDER PRODUCT, AND POWDER COMMODITY

(71) Applicant: A & H INTERNATIONAL COSMETICS CO., LTD, Shanghai (CN)

(72) Inventors: Yong Tian, Shanghai (CN); Jinhai Chen, Shanghai (CN); Bokchul Shin, Shanghai (CN); Jie Shen, Shanghai (CN); Yuncai Tian, Shanghai (CN); Tao Yu, Shanghai (CN)

(73) Assignee: A & H INTERNATIONAL COSMETICS CO., LTD, Shanghai (CN)

( * ) Notice: Subject to any disclaimer, the term of this patent is extended or adjusted under 35 U.S.C. 154(b) by 0 days.

(21) Appl. No.: 19/021,046

(22) Filed: Jan. 14, 2025

Related U.S. Application Data

(63) Continuation of application No. PCT/CN2023/122321, filed on Sep. 27, 2023.

(30) Foreign Application Priority Data

Feb. 14, 2023 (CN) .......................... 202310120492.7

(51) Int. Cl.
*A61K 8/02* (2006.01)
*A61K 8/25* (2006.01)
*A61K 8/58* (2006.01)
*A61K 8/891* (2006.01)
*A61Q 19/00* (2006.01)

(52) U.S. Cl.
CPC .............. *A61K 8/022* (2013.01); *A61Q 19/00* (2013.01); *A61K 2800/522* (2013.01); *A61K 2800/592* (2013.01); *A61K 2800/84* (2013.01)

(58) Field of Classification Search
None
See application file for complete search history.

(56) References Cited

U.S. PATENT DOCUMENTS

2010/0203097 A1* 8/2010 Tanaka ................... A61K 8/025
  424/401
2022/0192932 A1* 6/2022 Zeng ..................... A61K 8/022

FOREIGN PATENT DOCUMENTS

| CN | 110897993 A | 3/2020 |
| CN | 111904871 A | 11/2020 |
| CN | 113304066 A | 8/2021 |
| CN | 114209605 A | 3/2022 |
| CN | 114557920 A | 5/2022 |
| CN | 115154335 A | 10/2022 |
| CN | 115252516 A | 11/2022 |
| CN | 116139023 A | 5/2023 |
| JP | 2019131482 A | 8/2019 |
| KR | 20120119330 A | 10/2021 |

OTHER PUBLICATIONS

International Search Report and Written Opinion dated Dec. 20, 2023 for International Application No. PCT/ CN2023/122321.
The Second Office Action dated Aug. 30, 2024 for Chinese Office Action No. 202310120492.7.
The First Office Action dated Dec. 14, 2023 for Chinese Office Action No. 202310120492.7.
Notification to Grant Patent Right for Invention dated Sep. 30, 2024 for Application No. 202310120492.7.

* cited by examiner

Primary Examiner — Brian Gulledge

(57) ABSTRACT

Provided are a preparation method for a powder product, a powder product, and a powder commodity. The preparation method for a powder product includes the following steps: mixing 30% to 50% by mass of an oil-phase component and 50% to 70% by mass of a water-phase component to form a powder mixture liquid, feeding the powder mixture liquid into a mold, and baking the powder mixture liquid until its moisture content is ≤20%, to obtain a powder base product; cooling the powder base product to a predetermined temperature to obtain a solidified powder base product; releasing the solidified powder base product from the mold, and vacuum freeze-drying under a vacuum negative pressure condition. The powder product obtained by the freeze-drying is less prone to cakey makeup or powder floating, has a lighter and thinner skin feeling, and is fitter to skin.

3 Claims, No Drawings

PREPARATION METHOD FOR POWDER PRODUCT, POWDER PRODUCT, AND POWDER COMMODITY

CROSS REFERENCE TO RELATED APPLICATION

The present application is a continuation of International Application No. PCT/CN2023/122321, filed on Sep. 27, 2023, which claims priority to Chinese Patent Application No. 202310120492.7, entitled "PREPARATION METHOD FOR POWDER PRODUCT, POWDER PRODUCT, AND POWDER COMMODITY" filed on Feb. 14, 2023, both of which are incorporated herein by reference in their entireties.

TECHNICAL FIELD

The present application belongs to the technical field of daily cosmetics, and specifically relates to a preparation method for a powder product, a powder product, and a powder commodity.

BACKGROUND

Powder products, such as eye shadow, powder blusher, and pressed powder, are popular among women who want to be beautiful, and have become one of the most commonly-used beauty products for women's makeup and touch-ups.

A conventional production process for powder products is powder pressing or baking. Powder pressing means pressing particles together. Powder-pressed products have a relatively strong particle feeling, but slightly poor fitness, which results in makeup separation. Powder floats and flies during powder pressing, and may cause coughing, sneezing and the like in users who are allergic to powder. Main raw materials for preparing powder-baked products are minerals, which need to be finely ground during preparation, even by for example rolling. Clay is one of the main raw materials, with high fitness but slightly poor color rendering.

SUMMARY

In view of this, the present application provides a preparation method for a powder product, a powder product, and a powder commodity, to improve the skin feeling and moisture retention of the powder product.

In a first aspect, an embodiment of the present application provides a preparation method for a powder product, including the following steps:

mixing 30% to 50% by mass of an oil-phase component and 50% to 70% by mass of a water-phase component to form a powder mixture liquid, where based on a total weight of the powder mixture liquid, the oil-phase component includes 28.85% to 48.8% of a filler, 0.1% to 1% of an emollient, and 0.05% to 0.2% of an antioxidant, and the water-phase component includes 53.7% to 68.9% of a solvent, 0.5% to 3% of a moisturizer, 0.5% to 2% of an emulsifier, 0.1% to 0.5% of a thickener, and 0.05% to 0.8% of a preservative; feeding the powder mixture liquid into a mold, and baking the powder mixture liquid until its moisture content is ≤20%, to obtain a powder base product; cooling the powder base product to a predetermined temperature to obtain a solidified powder base product, wherein the predetermined temperature is lower than a consolute temperature of the powder base product; releasing the solidified powder base product from the mold, and vacuum freeze-drying under a vacuum negative pressure condition to obtain the powder product with a water content of 2% to 5%, where the vacuum freeze-drying includes pre-freezing, sublimation drying and desorption drying.

According to the embodiment of the first aspect of the present application, the baking specifically includes baking at a temperature of 35° C. to 55° C. for 1 to 2 hours.

According to the embodiment of the first aspect of the present application, the vacuum negative pressure condition specifically includes: maintaining negative pressure at −0.3 mpa to −0.6 mpa in an initial state of vacuum.

According to the embodiment of the first aspect of the present application, the pre-freezing specifically includes freezing at −40° C. to −50° C. for 0.5 to 2 hours.

According to the embodiment of the first aspect of the present application, the sublimation drying includes: heating the solidified powder base product to a temperature of −3° C. to 3° C., where the heating includes a plurality of first heating stages and a plurality of first heat preservation stages, the first heating stages and the first heat preservation stages are alternately carried out; the heating rate in the first heating stages is 0.5 to 1° C./min for 10 to 20 minutes, and the first heat preservation time is 1.5 to 2 hours.

According to the embodiment of the first aspect of the present application, the desorption drying includes: drying the solidified powder base product at 20° C. to 60° C., where the drying includes a plurality of second heating stages and a plurality of second heat preservation stages, the second heating stages and the second heat preservation stages are alternately carried out; the heating rate in the second heating stages is 0.5 to 1° C./min for 10 to 20 minutes, and the second heat preservation time is 1.5 to 2 hours.

According to the embodiment of the first aspect of the present application, the oil-phase component satisfies one or more of the following conditions:

the filler is selected from modified starch, synthetic fluorphlogopite, sericite, talc powder, silica, polymethyl methacrylate, dimethicone/vinyl dimethicone crosspolymer, vinyl dimethicone/methicone silsesquioxane crosspolymer, dimethicone crosspolymer, boron nitride, organosilicon elastomer, calcium carbonate, pearl powder, silk powder, zinc stearate, aluminum stearate, lauroyl lysine, polymethyl silsesquioxane, kaolin, nylon-12, diamond powder, zinc oxide, barium sulfate, hydroxyapatite, aluminum oxide, bismuth oxychloride, aluminum hydroxide, magnesium myristate, nephrite powder, or a combination thereof;

the emollient is selected from polydimethylsiloxane and derivatives thereof, triglycerides and derivatives thereof, jojoba oil, sunflower seed oil, castor oil, coconut oil, grape seed oil, shea butter, meadowfoam seed oil, macadamia nut oil, olive oil, palm oil, squalane, cocoa butter, jojoba fat, glycolipids, octyldodecanol, caprylic/capric triglycerides, coconut alcohol-caprylic/capric triglycerides, oleic/linoleic/linolenic polyglycerin esters, dioctyldodecanol dimer dilinoleate, or a combination thereof; and the antioxidant is selected from pentaerythritol tetraethylhexanoate, vitamin C, vitamin C glucoside, vitamin C acetate, tocopherol, tocopherol acetate, ascorbyl palmitate, retinol palmitate, or a combination thereof.

According to the embodiment of the first aspect of the present application, the water-phase component satisfies one or more of the following conditions:

the solvent is selected from deionized water, plant fermentation broth, plant flower water, or a combination thereof;

the moisturizer is selected from glycerin, sodium hyaluronate, 1,3-propanediol, 1,2-hexanediol, trehalose, tremella polysaccharides, saccharide isomerate, betaine, urea, or a combination thereof;

the emulsifier is selected from polysorbate, sorbitan sesquiisostearate, or a combination thereof;

the thickener is selected from tara gum, cellulose gum, microcrystalline cellulose, guar gum, Arabic gum, gellan gum, carrageenan, or a combination thereof; and the preservative is selected from phenoxyethanol, p-hydroxyacetophenone, 1,2-pentanediol, 1,2-hexanediol, paraanisic acid, caprylyl glycol, ethylhexylglycerin, benzoic acid, sodium benzoate, octanoyl hydroxamic acid, chlorphenesin, or a combination thereof.

In a second aspect, an embodiment of the present application provides a powder product prepared by any of the aforementioned methods.

In a third aspect, an embodiment of the present application provides a powder commodity, including a packaging box and the aforementioned powder product.

Compared with related technologies, the present application has at least the following beneficial effects:

According to the preparation method for a powder product provided in the present application, the powder mixture liquid is solidified by freeze-drying to obtain the powder product (such as eye shadow, powder blusher, or pressed powder) that is less prone to phenomena such as cakey makeup or powder floating or flying. Meanwhile, because the deionized water is volatilized by freeze-drying and the oil-phase component is retained, the powder product has a lighter and thinner skin feeling and is fitter to skin.

DETAILED DESCRIPTION

In order to make the application objectives, technical solutions, and beneficial technical effects of the present application clearer, the present application will be further explained in detail below in conjunction with the embodiments. It should be understood that the embodiments described in this specification are merely intended to interpret the present application, but not intended to limit the present application.

For the sake of simplicity, the present application only explicitly discloses some numerical ranges. However, any lower limit can be combined with any upper limit to form an unspecified range; any lower limit can be combined with other lower limits to form an unspecified range, and any upper limit can be combined with any other upper limit to form an unspecified range. Moreover, although not explicitly specified, each point or single value between the endpoints of a range is included in the range. Therefore, each point or single value can be combined as lower limit or upper limit with any other point or single value, or combined with other lower limit or upper limit, to form an unspecified range.

In the description of the present application, it should be noted that unless otherwise specified, "above" and "below" mean to include the corresponding value, and "more" in "one or more" means two or more.

The above summary of the present application is not intended to describe every disclosed implementation or every implementation in the present application. The following description illustrates exemplary implementations more specifically. In many places throughout the application, guidance is provided through a series of examples, which can be used in various combinations. In each example, the list in enumeration is only a representative group and should not be interpreted as exhaustive.

The term "bond" used herein includes but is not limited to chemical bonds such as chemical absorption and covalent bonds. The term "bonding" can be interpreted likewise accordingly.

With the increasing improvement of people's living standards, there is higher requirements for makeup powder products. A conventional production process for powder products is powder pressing or baking. Powder pressing means pressing particles together. Powder-pressed products have a relatively strong particle feeling, but slightly poor fitness, which results in makeup separation. Powder floats and flies during powder pressing, and may cause coughing, sneezing and the like in users who are allergic to powder. Main raw materials for preparing powder-baked products are minerals, which need to be finely ground during preparation, even by for example rolling. Clay is one of the main raw materials, with high fitness but slightly poor color rendering.

Through inventors' research, a preparation method for a powder product is provided, where a powder mixture liquid is solidified by freeze-drying to obtain the powder product (such as eye shadow, powder blusher, or pressed powder) that is less prone to cakey makeup or powder floating/flying. Meanwhile, because deionized water is volatilized by freeze-drying and an oil-phase component is retained, the powder product has a lighter and thinner skin feeling and is fitter to skin.

Preparation Method for a Powder Product

In a first aspect, an embodiment of the present application provides a preparation method for a powder product, including the following steps:

mixing 30% to 50% by mass of an oil-phase component and 50% to 70% by mass of a water-phase component to form a powder mixture liquid, where based on a total weight of the powder mixture liquid, the oil-phase component includes 28.85% to 48.8% of a filler, 0.1% to 1% of an emollient, and 0.05% to 0.2% of an antioxidant, and the water-phase component includes 53.7% to 68.9% of a solvent, 0.5% to 3% of a moisturizer, 0.5% to 2% of an emulsifier, 0.1% to 0.5% of a thickener, and 0.05% to 0.8% of a preservative;

feeding the powder mixture liquid into a mold, and baking the powder mixture liquid until its moisture content is ≤20%, to obtain a powder base product;

cooling the powder base product to a predetermined temperature to obtain a solidified powder base product, where the predetermined temperature is lower than a consolute temperature of the powder base product;

releasing the solidified powder base product from the mold, and vacuum freeze-drying under a vacuum negative pressure condition to obtain the powder product with a water content of 2% to 5%, where the vacuum freeze-drying includes pre-freezing, sublimation drying and desorption drying.

In the present application document, the consolute temperature refers to a maximum temperature at which a solution completely freezes and solidifies. For a solution, the freezing and solidification point is a point at which the melting starts, so it is also known as co-melting point temperature.

The sublimation drying in the present application document can be understood as a drying process including the steps of rapidly freezing a material to be dried and then sublimating ice therein under high vacuum conditions into water vapor for removal. The sublimation of ice takes away heat, so that the entire freeze-drying process remains in a low-temperature frozen state, which is beneficial to retaining the activity of some substances.

The desorption drying in the present application document can be understood as a drying process including the steps of placing a material to be dried under negative pressure or vacuum conditions, and appropriately heating the material to reach a boiling point under negative pressure or solidifying the material by cooling and then controlling the melting point to dry the material.

In the present application, 30% to 50% of the oil-phase component and 50% to 70% of the water-phase component are mixed to form a powder mixture liquid, and then the powder mixture liquid is mixed, wherein the components in a suitable proportion are mixed for vacuum freeze-drying to obtain a finished powder product, such as eye shadow, powder blusher, or pressed powder. Therefore, the preparation method is simple and easy to operate, and suitable for batch production. Meanwhile, the obtained powder product is less prone to phenomena such as cakey makeup or powder floating or flying. In addition, because the deionized water is volatilized by freeze-drying and the oil-phase component is retained, the powder product has a lighter and thinner skin feeling and a better moisturizing effect and is fitter to skin. Moreover, the vacuum freeze-drying is carried out at a low temperature, which can furthest retain the components, color, and aroma of the starting materials.

By using the method provided in the embodiments of the present application to prepare powder products, many spherical powders can be added to achieve a stronger sense of lightness and absence of powdery feeling, whereas in the powder baking and pressing processes, many spherical powders cannot be added, otherwise powder products cannot be formed.

According to the embodiments of the present application, the consolute temperature of the powder mixture liquid is considered in the setting of the predetermined temperature. The predetermined temperature that is lower than the consolute temperature of the powder mixture liquid can ensure that the powder mixture liquid solidifies or crystallizes completely. By testing, the consolute temperature of the powder base product in the embodiments of the present application is about −30° C. In some embodiments, the predetermined temperature is −60° C. to −40° C. By controlling the predetermined temperature within the above range, the time for entire drying or heating can be comprehensively shortened to improve efficiency.

By the sublimation drying and the desorption drying, more than 95% of water can be removed from the powder mixture liquid, so that the obtained powder product is loose, porous, finer and smoother, and fitter to skin. When dried at low temperatures, the loss of some volatile components in the mixture are very small, which allows more room for product formulation design and enables product production from a wider range of raw materials. Due to drying in a frozen state, the volume is almost unchanged, and the original structure is maintained without concentration. The freeze-drying ensures the loose and porous properties of the powder product, making the powder finer and smoother and fitter to skin.

When dried at low temperatures, the loss of some volatile components in the material are very small, which allows more room for product formulation design and enables product production from a wider range of raw materials. Due to drying in a frozen state, the volume is almost unchanged, and the original structure is maintained without concentration.

In some embodiments, the feeding temperature is 50° C. to 100° C. The inventors of the present application have found by experiments that feeding at a temperature in this range can evenly transfer the powder mixture liquid into the mold.

The mold may be selected according to actual needs. The cross-section of the mold in the direction perpendicular to the thickness of the formed pressed powder may be in various shapes, such as square, round or triangular.

In the step of cooling the powder base product to the predetermined temperature, the powder base product may be cooled in a liquid nitrogen freezing tunnel at a temperature of −10° C. to 25° C. for 3 to 10 minutes, so the powder base product is solidified in the mold to facilitate subsequent delivery.

In the baking step, a constant temperature heating device such as a drying room or a constant temperature oven may be used for baking to remove some water or moisture, so that the powder mixture liquid has a higher density, which may avoid too excessive sponginess of the mixture after drying is solved, and may shorten the freeze-drying time and reduce process energy consumption.

In some embodiments, the baking specifically includes baking at a temperature of 35° C. to 55° C. for 1 to 2 hours. Such low-temperature baking under this condition can avoid the deactivation of thermosensitive components at high temperatures, and ensure that the powder mixture liquid has a suitable water content or moisture content for subsequent processing while the obtained powder product has suitable looseness.

In the embodiments of the present application, an automatic mold release machine or manual mold release may be used.

In some embodiments, the vacuum negative pressure condition specifically includes: maintaining negative pressure at −0.3 mpa to −0.6 mpa in an initial state of vacuum. Maintaining negative pressure at −0.3 mpa to −0.6 mpa is conducive to the smooth process of vacuum drying.

In some embodiments, the pre-freezing specifically includes freezing at −40° C. to −50° C. for 0.5 to 2 hours.

According to the embodiment of the first aspect of the present application, the sublimation drying includes: heating the solidified powder base product to a temperature of −3° C. to 3° C., where the heating includes a plurality of first heating stages and a plurality of first heat preservation stages, the first heating stages and the first heat preservation stages are alternately carried out; the heating rate in the first heating stages is 0.5 to 1° C./min for 10 to 20 minutes, and the first heat preservation time is 1.5 to 2 hours.

By controlling the heating rate of each heating stage in the range of 0.25 to 0.5° C./min and the time of each heating stage in the range of 10 to 15 minutes to achieve slow heating, issues on the sublimation interface are reduced, and the drying effect can be improved. By applying the heating process at above temperatures, the principle of full drying layer by layer in vacuum drying can be used to further improve the drying effect of a freeze-dried facial mask, reduce the water content, and ensure the drying efficiency.

In the embodiments of the present application, the water in the first heating and the heat preservation stages during this period is removed in a form of ice crystals, and both the sublimation interface pressure and the temperature for forming a freeze-dried layer in the powder base product must be controlled so that the temperature is lower than the consolute point of the product to prevent ice crystals from melting. But for adsorbed water, its adsorption energy is high, and if insufficient energy is provided, water cannot be desorbed from the adsorption state. The temperature should be sufficiently high, as long as it does not exceed the maximum allowable temperature, does not result in a damage of the product, and does not cause denaturation of the product due to overheating. Meanwhile, in order to provide sufficient driving force for the desorbed water vapor to escape the product, a relatively large vapor pressure difference must be formed between inside and outside the product, so a relatively high degree of vacuum must be maintained during this period. The residual water content may generally be controlled between 0.5% and 4%.

According to an embodiment of the first aspect of the present application, the desorption drying includes: drying the solidified powder base product at 20° C. to 60° C., where the drying includes a plurality of second heating stages and a plurality of second heat preservation stages, the second heating stages and the second heat preservation stages are alternately carried out; the heating rate in the second heating stages is 0.5 to 1° C./min for 10 to 20 minutes, and the second heat preservation time is 1.5 to 2 hours.

By controlling the heating rate of each heating stage in a range of 0.25 to 0.5° C./min and the time of each heating stage in the range of 10 to 15 minutes to achieve slow heating, issues on the sublimation interface are reduced, and the drying effect can be improved. By applying the heating process at above temperatures, the principle of full drying layer by layer in vacuum drying can be used to further improve the drying effect of a freeze-dried facial mask, reduce the water content, and ensure the drying efficiency.

Through heating in the above heating stages (with the temperature difference) and appropriate heat preservation, the second stages mainly focus on efficiency, without affecting the properties of active substances in the powder product.

In some embodiments, the filler is selected from modified starch, synthetic fluorphlogopite, sericite, talc powder, silica, polymethyl methacrylate, dimethicone/vinyl dimethicone crosspolymer, vinyl dimethicone/methicone silsesquioxane crosspolymer, dimethicone crosspolymer, boron nitride, organosilicon elastomer, calcium carbonate, pearl powder, silk powder, zinc stearate, aluminum stearate, lauroyl lysine, polymethyl silsesquioxane, kaolin, nylon-12, diamond powder, zinc oxide, barium sulfate, hydroxyapatite, aluminum oxide, bismuth oxychloride, aluminum hydroxide, magnesium myristate, nephrite powder, or a combination thereof.

In some embodiments, the filler has a particle size of 5 μm to 10 μm. According to the embodiments of the present application, an excessively small particle size is prone to agglomeration, whereas an excessively large particle size increases graininess.

In some embodiments, the emollient is selected from polydimethylsiloxane and derivatives thereof, triglycerides and derivatives thereof, jojoba oil, sunflower seed oil, castor oil, coconut oil, grape seed oil, shea butter, meadowfoam seed oil, macadamia nut oil, olive oil, palm oil, squalane, cocoa butter, jojoba fat, glycolipids, octyldodecanol, caprylic/capric triglycerides, coconut alcohol-caprylic/capric triglycerides, oleic/linoleic/linolenic polyglycerin esters, dioctyldodecanol dimer dilinoleate, or a combination thereof.

In some embodiments, the antioxidant is selected from pentaerythritol tetraethylhexanoate, vitamin C, vitamin C glucoside, vitamin C acetate, tocopherol, tocopherol acetate, ascorbyl palmitate, retinol palmitate, or a combination thereof.

In some embodiments, the solvent is selected from deionized water, plant fermentation broth, plant flower water, or a combination thereof.

In some embodiments, the moisturizer is selected from glycerin, sodium hyaluronate, 1,3-propanediol, 1,2-hexanediol, trehalose, tremella polysaccharides, saccharide isomerate, betaine, urea, or a combination thereof.

In some embodiments, the emulsifier is selected from polysorbate, sorbitan sesquiisostearate, or a combination thereof.

In some embodiments, the thickener is selected from tara gum, cellulose gum, microcrystalline cellulose, guar gum, Arabic gum, gellan gum, carrageenan, or a combination thereof.

In some embodiments, the preservative is selected from phenoxyethanol, p-hydroxyacetophenone, 1,2-pentanediol, 1,2-hexanediol, paraanisic acid, caprylyl glycol, ethylhexylglycerin, benzoic acid, sodium benzoate, octanoyl hydroxamic acid, chlorphenesin, or a combination thereof.

Powder Product

In a second aspect, an embodiment of the present application provides a powder product prepared by any of the aforementioned methods. The powder product provided in the present application includes eye shadow, powder blusher, and pressed powder. The powder product is less prone to phenomena such as cakey makeup or powder floating or flying. In addition, because the deionized water is volatilized by freeze-drying and the oil-phase component is retained, the powder product has a lighter and thinner skin feeling and is fitter to skin. Moreover, the vacuum freeze-drying is carried out at a low temperature, which can furthest retain the components, color, and aroma of the starting materials.

Powder Commodity

In a third aspect, an embodiment of the present application provides a powder commodity, including a packaging box and the aforementioned powder product. The powder product is embedded in the packaging box to obtain the powder commodity for commercial sales.

Some exemplary embodiments of the present invention are provided as follows.

Embodiment 1. A preparation method for a powder product, comprising the following steps:

mixing 30% to 50% by mass of an oil-phase component and 50% to 70% by mass of a water-phase component to form a powder mixture liquid, wherein based on a total weight of the powder mixture liquid, the oil-phase component comprises 28.85% to 48.8% of a filler, 0.1% to 1% of an emollient, and 0.05% to 0.2% of an antioxidant, and the water-phase component comprises 53.7% to 68.9% of a solvent, 0.5% to 3% of a moisturizer, 0.5% to 2% of an emulsifier, 0.1% to 0.5% of a thickener, and 0.05% to 0.8% of a preservative;

feeding the powder mixture liquid into a mold, and baking the powder mixture liquid until its moisture content is ≤20%, to obtain a powder base product;

cooling the powder base product to a predetermined temperature to obtain a solidified powder base product, wherein the predetermined temperature is lower than a consolute temperature of the powder base product; and releasing the solidified powder base product from the mold, and vacuum freeze-drying under a vacuum negative pressure condition to obtain the powder product with a water content of 2% to 5%, wherein the vacuum freeze-drying comprises pre-freezing, sublimation drying and desorption drying.

Embodiment 2. The preparation method for the powder product according to Embodiment 1, wherein the baking specifically comprises baking at a temperature of 35° C. to 55° C. for 1 to 2 hours.

Embodiment 3. The preparation method for the powder product according to Embodiment 1, wherein the vacuum negative pressure condition specifically comprises: maintaining negative pressure at −0.3 mpa to −0.6 mpa in an initial state of vacuum.

Embodiment 4. The preparation method for the powder product according to Embodiment 1, wherein the pre-freezing specifically comprises freezing at −40° C. to −50° C. for 0.5 to 2 hours.

Embodiment 5. The preparation method for the powder product according to Embodiment 1, wherein the sublimation drying comprises: heating the solidified powder base product to a temperature of −3° C. to 3° C., wherein the heating comprises a plurality of first heating stages and a plurality of first heat preservation stages, the first heating stages and the first heat preservation stages are alternately carried out; a heating rate in the first heating stages is 0.5 to 1° C./min for 10 to 20 minutes, and a first heat preservation time is 1.5 to 2 hours.

Embodiment 6. The preparation method for the powder product according to Embodiment 1, wherein the desorption drying comprises: drying the solidified powder base product at 20° C. to 60° C., wherein the drying comprises a plurality of second heating stages and a plurality of second heat preservation stages, the second heating stages and the second heat preservation stages are alternately carried out; a heating rate in the second heating stages is 0.5 to 1° C./min for 10 to 20 minutes, and a second heat preservation time is 1.5 to 2 hours.

Embodiment 7. The preparation method for the powder product according to Embodiment 1, wherein the oil-phase component satisfies one or more of the following conditions:
the filler is selected from modified starch, synthetic fluorphlogopite, sericite, talc powder, silica, polymethyl methacrylate, dimethicone/vinyl dimethicone crosspolymer, vinyl dimethicone/methicone silsesquioxane crosspolymer, dimethicone crosspolymer, boron nitride, organosilicon elastomer, calcium carbonate, pearl powder, silk powder, zinc stearate, aluminum stearate, lauroyl lysine, polymethyl silsesquioxane, kaolin, nylon-12, diamond powder, zinc oxide, barium sulfate, hydroxyapatite, aluminum oxide, bismuth oxychloride, aluminum hydroxide, magnesium myristate, nephrite powder, or a combination thereof;
the emollient is selected from polydimethylsiloxane and derivatives thereof, triglycerides and derivatives thereof, jojoba oil, sunflower seed oil, castor oil, coconut oil, grape seed oil, shea butter, meadowfoam seed oil, macadamia nut oil, olive oil, palm oil, squalane, cocoa butter, jojoba fat, glycolipids, octyldodecanol, caprylic/capric triglycerides, coconut alcohol-caprylic/capric triglycerides, oleic/linoleic/linolenic polyglycerin esters, dioctyldodecanol dimer dilinoleate, or a combination thereof; and
the antioxidant is selected from pentaerythritol tetraethylhexanoate, vitamin C, vitamin C glucoside, vitamin C acetate, tocopherol, tocopherol acetate, ascorbyl palmitate, retinol palmitate, or a combination thereof.

Embodiment 8. The preparation method for the powder product according to Embodiment 1, wherein the water-phase component satisfies one or more of the following conditions:
the solvent is selected from deionized water, plant fermentation broth, plant flower water, or a combination thereof;
the moisturizer is selected from glycerin, sodium hyaluronate, 1,3-propanediol, 1,2-hexanediol, trehalose, tremella polysaccharides, saccharide isomerate, betaine, urea, or a combination thereof;
the emulsifier is selected from polysorbate, sorbitan sesquiisostearate, or a combination thereof;
the thickener is selected from tara gum, cellulose gum, microcrystalline cellulose, guar gum, Arabic gum, gellan gum, carrageenan, or a combination thereof, and
the preservative is selected from phenoxyethanol, p-hydroxyacetophenone, 1,2-pentanediol, 1,2-hexanediol, paraanisic acid, caprylyl glycol, ethylhexylglycerin, benzoic acid, sodium benzoate, octanoyl hydroxamic acid, chlorphenesin, or a combination thereof.

Embodiment 9. A powder product prepared by the method according to any one of Embodiments 1-8.

Embodiment 10. A powder commodity, comprising a packaging box and the powder product according to Embodiment 9.

EXAMPLES

The following examples more specifically describe the content disclosed in the present application. These examples are only used for explanatory description, because various modifications and changes made within the scope of the content disclosed in the present application are apparent to those skilled in the art. Unless otherwise stated, all parts, percentages, and ratios described in the following examples are based on weight, and all reagents used in the examples are commercially available or synthesized according to conventional methods and can be directly used without further treatment, and all instruments used in the examples are commercially available.

Polysorbate: purchased from Ashland Corporation (Tween 80, Tween 60).

Sorbitan sesquiisostearate: purchased from Croda China (SPAN 60).

Vinyl dimethicone/methicone silsesquioxane crosspolymer: purchased from Developed Technologies (average particle size 5-10 μm).

Composition of caprylyl glycol and ethylhexylglycerin: purchased from Ashland Corporation.

Silica: purchased from SUNJIN BEAUTY SCIENCE CO., LTD.

Mica: purchased from Anhui Henghao Technology Co., Ltd.

Composition of mica/zinc oxide/hydroxyapatite: purchased from Sanhao Cosmetics Materials Co., Ltd.

Boron nitride: purchased from Weifang Chunfeng New Material Technology Co., Ltd.

Fluorophlogopite: purchased from Anhui Gerui Mining Co., Ltd.

Example 1

Ingredients and their amounts of raw materials for a powder product are shown in Table 1.

TABLE 1

| | INCI name of raw materials | Added mass percentage, % |
|---|---|---|
| Water-phase component | Deionized water | 56.65 |
| | Glycerin | 1.2 |
| | Tween 60 | 1 |
| | Gellan gum | 0.1 |
| | Carrageenan | 0.25 |
| | Chlorphenesin | 0.1 |
| | Composition of caprylyl glycol and ethylhexylglycerin | 0.4 |
| Oil-phase component | Polymethyl methacrylate | 8 |
| | Vinyl dimethicone/ methicone silsesquioxane crosspolymer | 6 |
| | Silica | 17 |
| | Nylon-12 | 2.8 |
| | Boron nitride | 1 |
| | Lauroyl lysine | 0.5 |
| | Composition of mica/ zinc oxide/ hydroxyapatite | 0.4 |
| | Aluminum oxide | 2 |
| | Bismuth oxychloride | 2 |
| | Squalane | 0.5 |
| | Vitamin C acetate | 0.05 |
| | Pentaerythritol tetraethylhexoate | 0.05 |

Pre-treatment: 1) Performing a surface hydrophobic treatment on silica in the oil-phase filler, using triethoxycaprylylsilane or polydimethylsiloxane (dimethicone) as a treatment agent in an amount of 2% to 5%. First, the treatment agent was mixed with silica, followed by baking at a high temperature of 100° C. to 120° C. for 4 to 6 hours, to obtain the treated silica with a good hydrophobic effect.

2) Pre-dispersing the water-phase thickener in glycerin and a part of deionized water, and after dispersion, formulating the water phase.

Preparation of a powder mixture liquid: Mixing the water-phase and oil-phase combinations separately, adding the oil phase to the water phase in a homogeneous state at 70° C. to 85° C., keeping the mixture homogeneous for 10 to 20 minutes, standing at room temperature, and discharging.

A freeze-drying process of the powder mixture liquid was as follows:

S1: feeding at a temperature of 50° C. to 100° C.;

S2: cooling in a freezing tunnel at a temperature of −10° C. to 25° C. for 3 to 10 minutes;

S3: baking in a constant temperature heating device such as a drying room or a constant temperature oven at 45° C. for 2 hours until a water content of 15%;

S4: freezing in a liquid nitrogen tunnel at −45° C. for 1 to 2 hours; S5: mold-releasing;

S6: pre-freezing procedure: freezing in a freeze dryer at −45° C. for 0.5 to 2 hours;

S7: sublimation drying: in the freeze dryer under negative pressure conditions (not more than 5 MPa), heating from −45° C. (the temperature in the previous step) for 2 hours per step of 10° C., with a total duration of about 12 hours; and S8: desorption drying: in the freeze dryer at 25° C. for 2 hours, heating three times by 10° C. (i.e. heating three times to the temperatures of 35° C., 45° C., and 55° C., respectively) and drying for 2 hours per step (each time).

Example 2

Ingredients and their amounts of raw materials for a powder product are shown in Table 2.

TABLE 2

| | INCI name of raw materials | Added mass percentage, % |
|---|---|---|
| Water-phase component | Deionized water | 54.55 |
| | Trehalose | 1.5 |
| | Tween 80 | 1.5 |
| | Arabic gum | 0.3 |
| | Tara gum | 0.05 |
| | Chlorphenesin | 0.1 |
| | Composition of caprylyl glycol and ethylhexylglycerin | 0.4 |
| Oil-phase component | Polymethyl methacrylate | 8 |
| | Vinyl dimethicone/methicone silsesquioxane crosspolymer | 6 |
| | Talc powder | 18 |
| | Nylon-12 | 2.8 |
| | Boron nitride | 1 |
| | Lauroyl lysine | 0.5 |
| | Composition of mica/zinc oxide/hydroxyapatite | 0.4 |
| | Aluminum oxide | 2 |
| | Bismuth oxychloride | 2 |
| | Jojoba oil | 0.8 |
| | Vitamin C acetate | 0.05 |
| | Tocopherol | 0.05 |

Pre-treatment: 1) Performing a surface hydrophobic treatment on talc powder in the oil-phase filler, using triethoxycaprylylsilane or polydimethylsiloxane (dimethicone) as a treatment agent in an amount of 2% to 5%. First, the treatment agent was mixed with talc powder, followed by baking at a high temperature of 100° C. to 120° C. for 4 to 6 hours, to obtain the treated talc powder with a good hydrophobic effect.

2) Pre-dispersing the water-phase thickener in trehalose and a part of deionized water, and after dispersion, formulating the water phase.

Preparation of a powder mixture liquid: Mixing the water-phase and oil-phase combinations separately, adding the oil phase to the water phase in a homogeneous state at 70° C. to 85° C., keeping the mixture homogeneous for 10 to 20 minutes, standing at room temperature, and discharging.

A freeze-drying process for the powder mixture liquid was as follows:

A freeze-drying process for the powder mixture liquid was as follows:

S1: feeding at a temperature of 50° C. to 100° C.;

S2: cooling in a freezing tunnel at a temperature of −10° C. to 25° C. for 3 to 10 minutes;

S3: baking in a constant temperature heating device such as a drying room or a constant temperature oven at 45° C. for 2 hours until a water content of 13%;

S4: freezing in a liquid nitrogen tunnel at −45° C. for 1 to 2 hours; S5: mold-releasing;

S6: pre-freezing procedure: freezing in a freeze dryer at −45° C. for 0.5 to 2 hours;

S7: sublimation drying: in the freeze dryer under negative pressure conditions (not more than 5 MPa), heating from −45° C. (the temperature in the previous step), for 2 hours per step of 10° C., with a total duration of about 12 hours; and S8: desorption drying: in the freeze dryer at 25° C. for 2 hours, heating three times by 10° C. (i.e. heating three times to the temperatures of 35° C., 45° C., and 55° C., respectively) and drying for 2 hours per step (each time).

Comparative Example 1

Ingredients and their amounts of raw materials for a powder product are shown in Table 3.

TABLE 3

| INCI name of raw materials | Added mass percentage, % |
|---|---|
| Mica, triethoxyoctylsilane (mass ratio 97%:3%) | 49.8 |
| Synthetic fluorophlogopite, triethoxyoctylsilane (mass ratio 97%:3%) | 20 |
| Silica, triethoxyoctylsilane (mass ratio 97%:3%) | 5 |
| Corn starch | 3 |
| Polymethyl silsesquioxane | 3 |
| Boron nitride, triethoxyoctylsilane (mass ratio 97%:3%) | 3 |
| Synthetic wax | 5 |
| Magnesium stearate | 2 |
| Polymethylsiloxane | 7 |
| Diisostearyl alcohol malate | 1 |
| Phenoxyethanol | 1.2 |

All the powder raw materials in the above mass percentages were mixed, and added into a powdering pot for powdering 2 minutes at a speed of 10000 r/min; then the oil and preservative were added for powdering 2 minutes at a speed of 10000 r/min; followed by mixing and pressing the powder.

Comparative Example 2

Ingredients and their amounts of raw materials for a powder product are shown in Table 4.

TABLE 4

| INCI name of raw material | Added mass percentage, % |
|---|---|
| Dimethicone/vinyl dimethicone | 2.63 |
| Silica | 7 |
| Synthetic fluorophlogopite, triethoxyoctylsilane (mass ratio 97%:3%) | 17 |
| Magnesium myristate modified synthetic fluorphlogopite | 18.51 |
| Mica | 8.78 |
| Phenoxyethanol | 0.9 |
| Water | 39 |
| Xanthan gum | 0.27 |
| Kaolin | 0.45 |
| Spermaceti-based PEG/PPG-10/1 polydimethylsiloxane | 1.26 |
| Polyglycerin-4 isostearate | 1.5 |
| Pentaerythritol tetraisostearate | 1.35 |
| Polydimethylsiloxane (dimethicone) | 0.45 |
| Glycerin | 0.45 |
| Butanediol | 0.45 |

Powder and oil were mixed, and the emulsifier was added. The mixture was stirred and homogenized thoroughly for dissolving. Then the water phase was added and the resulting mixture was homogenized for 15 minutes, and placed in a mold for baking at 60° C. for 24 hours. The baked product was subjected to powder pressing.

Test Section

1) Test on Mechanical Properties of Products pieces of powders (each piece of freeze-dried pressed powder 50 mg) prepared in each of Example 1, Example 2, Comparative Example 1 and Comparative Example 2, respectively, were taken and subjected to collision simulation: dropping 5 times freely at 0.6 m above the ground, and recording breakage ratios (calculation method for breakage ratios: for example, if 1 of the 5 pieces was broken after the $1^{st}$ drop, the breakage ratio was 1/5; if 3 of the 5 pieces were broken after the $2^{nd}$ drop, the breakage ratio was 3/5). The results are shown in Table 5.

TABLE 5

|  | $1^{st}$ drop | $2^{nd}$ drop | $3^{rd}$ drop | $4^{th}$ drop | $5^{th}$ drop |
|---|---|---|---|---|---|
| Breakage ratio in Example 1 | — | — | — | 1/5 | 2/5 |
| Breakage ratio in Example 2 | — | — | — | — | 1/5 |
| Breakage ratio in Comparative Example 1 | 2/5 | 5/5 | — | — | — |
| Breakage ratio in Comparative Example 2 | 1/5 | 3/5 | 5/5 | — | — |

It can be seen from Table 5 that one piece of the powder products prepared in Example 1 of the present application began to be broken after the 4th drop, one piece of the powder products prepared in Example 2 began to be broken after the 5th drop, whereas all the 5 pieces of freeze-dried pressed powder prepared in Comparative Example 1 were broken after the $2^{nd}$ drop, and all the 5 pieces of freeze-dried pressed powder prepared in Comparative Example 2 were broken after the $3^{rd}$ drop. It is evident that the powder products prepared in Examples 1 and 2 of the present application exhibited high anti-breaking performance.

2) Test on Hydrating/Moisturizing Performance of Products (Test on Degree of Moisturizing)

The water content of skin depends on internal and external factors. The ability of the stratum corneum to retain water varies greatly, with the water content varying from 10% to 60%. The water content of skin affects the formation of a mixed film of oil and water on the surface of the skin, and the film is protective and very important for preventing skin aging.

The water testing followed the principle that the dielectric constants of water and other substances change greatly, a capacitor changes with skin capacitance which is within a measurable range, and the water content of the skin can be measured accordingly.

Water content was measured by a CORNEOMETER-capacitance method and represented by setting a moisture measurement value (MMV) ranging from 0 to 150. Almost no current passed through the tested skin, so the test results were actually not affected by the polarization effect and ion conductivity, and the influence of active skin on the measurement results was eliminated.

MMV was greatly affected by environmental temperature and humidity, and was generally tested at 20° C. and 50% relative humidity, with excellent results.

Testing Method:

A moisture probe was pressed vertically against the surface of the skin, and the top of the probe was pressed back a certain distance. A spring inside the probe maintained a pressure of 0.16N at the top of the probe applied to the surface of the skin. Within one second, the host displayed the result with a prompt sound.

The front end of the inner side of the arm was selected as a testing site, and the testing sites were marked on the inner sides of the arms of 30 volunteer subjects after cleaning. The test area for applying the sample was 5×5 square centimeters, and the amount of the applied sample was 0.2 g. The subjects were sitting quietly in a constant temperature and humidity environment for 30 minutes, then blank values were measured at the testing sites with a Corneometer. Five fixed points in each area were measured in order and an average value was taken. During the test, a full-time technician applied the sample and started timing, and then MMV changes were measured at each predetermined time according to the testing method. A growth rate of water content of skin was calculated according to the following formula: the growth rate of water content of skin being MMV $\% = (MMV_t - MMV_0)/MMV_0 \times 100\%$.

$MMV_0$ was the MMV value of the skin before applying.

$MMV_t$ was the MMV value of the skin at the time t after applying. The results are shown in Table 6 below:

TABLE 6

Moisturizing effects in Examples 1 and 2 and Comparative Examples 1 and 2

| Time/min | Example 1 | Example 2 | Comparative Example 1 | Comparative Example 2 |
|---|---|---|---|---|
| 15 | 63.2% | 63.8% | 59.1% | 58.5% |
| 30 | 62.2% | 62.4% | 57.1% | 56.2% |
| 60 | 61.0% | 60.8% | 55.1% | 53.6% |
| 90 | 59.2% | 59.3% | 52.1% | 51.4% |
| 120 | 57.1% | 57.3% | 48.5% | 47.3% |

The results show that Examples 1 and 2 exhibited the relatively high water content of skin and high moisturizing intensity in the later stage, which may be due to the fact that water was lost through the freeze-drying only while retaining the effects of other components; while Comparative Example 1 and 2 exhibited the slightly low moisture content in the initial stage and poor moisturizing effect, which may be due to the fact that deep moisturization of the epidermal layer cannot be improved by adding components or reducing amounts of components and an immediate and long-lasting hydration was not achieved.

3) Usability of Powder Products 10 members of the cosmetics professionals in a team applied the powder products to the skin, to evaluate the usability on a 5-score scale for "lightness, smoothness, no powdery feeling, and color rendering (on the skin)" (very poor usability: 0 score; very good usability: 5 scores). An average evaluation value was calculated and determined as follows, and represented by symbols in Table 7.

[Determination]
⊚: The average score of the evaluation values is 4 or higher;
○: The average score of the evaluation values is 3 or higher and less than 4;
Δ: The average score of the evaluation values is 2 or higher and less than 3;
x: The average score of the evaluation values is less than 2;

TABLE 7

| | Item | Example 1 | Example 2 | Comparative Example 1 | Comparative Example 2 |
|---|---|---|---|---|---|
| Usability | Lightness, smoothness, no powdery feeling | ⊚ | ⊚ | ○ | ○ |
| | Color rendering | ⊚ | ⊚ | ○ | ⊚ |

The powder products obtained in Example 1 and Example 2 exhibited relatively excellent results in lightness, smoothness, and no powdery feeling. Comparative Example 1 shows a powdery feeling and particularly poor usability. Comparative Example 2 shows a poorer skin feeling.

It can be seen from the above that the powder products prepared by freeze-drying the mixture of oil-phase components and water-phase components in appropriate proportions have excellent performance in both usability and impact resistance.

Described above are merely specific implementations of the present application, but the protection scope of the present application is not limited thereto. Any skilled person who is familiar with this art would readily conceive of various equivalent modifications or substitutions within the technical scope of the disclosure of the present application, and these modifications or substitutions shall fall within the protection scope of the present application. Therefore, the protection scope of the present application shall be subject to the protection scope of the claims.

What is claimed is:

1. A preparation method for a powder product, comprising the following steps:
    mixing 30% to 50% by mass of an oil-phase component and 50% to 70% by mass of a water-phase component to form a powder mixture liquid, wherein based on a total weight of the powder mixture liquid, the oil-phase component comprises 28.85% to 48.8% of a filler, 0.1% to 1% of an emollient, and 0.05% to 0.2% of an antioxidant, and the water-phase component comprises 53.7% to 68.9% of a solvent, 0.5% to 3% of a moisturizer, 0.5% to 2% of an emulsifier, 0.1% to 0.5% of a thickener, and 0.05% to 0.8% of a preservative;
    feeding the powder mixture liquid into a mold, and baking the powder mixture liquid at a temperature of 35° C. to 55° C. for 1 to 2 hours until its moisture content is ≤20%, to obtain a powder base product;
    cooling the powder base product to a predetermined temperature to obtain a solidified powder base product, wherein the predetermined temperature is lower than a consolute temperature of the powder base product; and
    freezing the solidified powder base product in a freeze dryer at a temperature of −40° C. to −50° C. for 0.5 to 2 hours; and sublimation drying in the freeze dryer under negative pressure conditions by heating the solidified powder base product to a temperature of −3° C. to 3° C., wherein the heating comprises a plurality of first heating stages and a plurality of first heat preservation stages, the first heating stages and the first heat preservation stages are alternately carried out; a heating rate in the first heating stages is 0.5 to 1° C./min for 10 to 20 minutes, and a first heat preservation time is 1.5 to 2 hours;

desorption drying the solidified powder base product at a temperature of 20° C. to 60° C. to obtain the powder product with a water content of 2% to 5%, wherein the desorption drying comprises a plurality of second heating stages and a plurality of second heat preservation stages, the second heating stages and the second heat preservation stages are alternately carried out; a heating rate in the second heating stages is 0.5 to 1° C./min for 10 to 20 minutes, and a second heat preservation time is 1.5 to 2 hours.

2. The preparation method for the powder product according to claim 1, wherein the filler is selected from modified starch, synthetic fluorphlogopite, sericite, talc powder, silica, polymethyl methacrylate, dimethicone/vinyl dimethicone crosspolymer, vinyl dimethicone/methicone silsesquioxane crosspolymer, dimethicone crosspolymer, boron nitride, organosilicon elastomer, calcium carbonate, pearl powder, silk powder, zinc stearate, aluminum stearate, lauroyl lysine, polymethyl silsesquioxane, kaolin, nylon-12, diamond powder, zinc oxide, barium sulfate, hydroxyapatite, aluminum oxide, bismuth oxychloride, aluminum hydroxide, magnesium myristate, nephrite powder, or a combination thereof;

the emollient is selected from polydimethylsiloxane and derivatives thereof, triglycerides and derivatives thereof, jojoba oil, sunflower seed oil, castor oil, coconut oil, grape seed oil, shea butter, meadowfoam seed oil, macadamia nut oil, olive oil, palm oil, squalane, cocoa butter, jojoba fat, glycolipids, octyldodecanol, caprylic/capric triglycerides, coconut alcohol-caprylic/capric triglycerides, oleic/linoleic/linolenic polyglycerin esters, dioctyldodecanol dimer dilinoleate, or a combination thereof; and the antioxidant is selected from pentaerythritol tetraethylhexanoate, vitamin C, vitamin C glucoside, vitamin C acetate, tocopherol, tocopherol acetate, ascorbyl palmitate, retinol palmitate, or a combination thereof.

3. The preparation method for the powder product according to claim 1, wherein the solvent is selected from deionized water, plant fermentation broth, plant flower water, or a combination thereof;

the moisturizer is selected from glycerin, sodium hyaluronate, 1,3-propanediol, 1,2-hexanediol, trehalose, tremella polysaccharides, saccharide isomerate, betaine, urea, or a combination thereof;

the emulsifier is selected from polysorbate, sorbitan sesquiisostearate, or a combination thereof;

the thickener is selected from tara gum, cellulose gum, microcrystalline cellulose, guar gum, Arabic gum, gellan gum, carrageenan, or a combination thereof; and the preservative is selected from phenoxyethanol, p-hydroxyacetophenone, 1,2-pentanediol, 1,2-hexanediol, paraanisic acid, caprylyl glycol, ethylhexylglycerin, benzoic acid, sodium benzoate, octanoyl hydroxamic acid, or a combination thereof.

* * * * *